(12) United States Patent
Dorsey et al.

(10) Patent No.: US 9,259,419 B2
(45) Date of Patent: *Feb. 16, 2016

(54) COMPOSITIONS AND METHODS RELATING TO SOLENOPSINS AND THEIR USES IN TREATING NEUROLOGICAL DISORDERS AND ENHANCING PHYSICAL PERFORMANCE

(71) Applicant: SYNAPSIN PHARMACEUTICALS, INC., Mt. Pleasant, SC (US)

(72) Inventors: Denis Dorsey, Lexington, SC (US); Mark S. Kindy, Mount Pleasant, SC (US)

(73) Assignee: SYNAPSIN PHARMACEUTICALS, INC., Columbia, SC (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/968,049

(22) Filed: Aug. 15, 2013

(65) Prior Publication Data

US 2014/0086998 A1 Mar. 27, 2014

Related U.S. Application Data

(63) Continuation-in-part of application No. 12/307,459, filed as application No. PCT/US2007/073018 on Jul. 9, 2007, now Pat. No. 8,524,741.

(60) Provisional application No. 60/806,887, filed on Jul. 10, 2006.

(51) Int. Cl.
*A61K 31/445* (2006.01)
*C07D 211/12* (2006.01)
*A61K 35/64* (2015.01)

(52) U.S. Cl.
CPC .............. *A61K 31/445* (2013.01); *A61K 35/64* (2013.01); *C07D 211/12* (2013.01)

(58) Field of Classification Search
CPC ..... A61K 31/445; A61K 35/64; C07D 211/12
USPC ........................................................ 514/314
See application file for complete search history.

(56) References Cited

U.S. PATENT DOCUMENTS

| | | | |
|---|---|---|---|
| 4,910,209 A | 3/1990 | Rehmert et al. | |
| 5,075,320 A | 12/1991 | Rehmert et al. | |
| 5,098,914 A | 3/1992 | Rehmert et al. | |
| 5,744,346 A | 4/1998 | Chrysler et al. | |
| 6,369,078 B1 | 4/2002 | Bowen et al. | |
| 6,440,698 B1 | 8/2002 | Gurney et al. | |
| 6,713,248 B2 | 3/2004 | Roberts et al. | |
| 8,168,657 B2 | 5/2012 | Bowen et al. | |
| 8,524,741 B2 | 9/2013 | Dorsey et al. | |
| 2004/0171614 A1 | 9/2004 | Pissarnitski et al. | |
| 2004/0229913 A1 | 11/2004 | Emir et al. | |
| 2006/0148727 A1 | 7/2006 | Hendrix et al. | |

FOREIGN PATENT DOCUMENTS

| | | |
|---|---|---|
| AU | 2007272619 | 1/2014 |
| CA | 2657256 | 1/2008 |
| CN | 101594867 A | 12/2009 |
| EP | 2043642 | 4/2009 |
| EP | 13180929.5 | 4/2009 |
| JP | 2013-2219 | 5/2013 |
| JP | 5484049 | 2/2014 |
| WO | WO 90/07274 | 6/1990 |
| WO | WO 02/11712 | 2/2002 |
| WO | WO 03/047499 | 6/2003 |
| WO | WO 2008/008720 | 1/2008 |
| WO | WO 2008/051258 | 5/2008 |

OTHER PUBLICATIONS

Acquati, et al. The gene encoding DRAP (BACE2), a glycosylated transmembrane protein of the aspartic protease family, maps to the down critical region. FEBS Lett. 2000, 468:59-64.

Akiyama, et al. Inflammation and Alzheimer's disease. Neurobiol. Aging. 2000, 21(3):383-421.

Aetna InteliHealth. Alzheimer's Disease. Last Updated on Dec. 12, 2007. Downloaded on Jul. 1, 2008, available at http://www.intelihealth.com/IH/ihtIH/WSIHW000/8303/9117/195703.html?d=dmtHealthAZ (4 pages).

Ant Pheromone May Aid Alzheimer's Patients. Science Daily. Posted on Feb. 4, 1998. Downloaded on Apr. 11, 2013 at http://www.sciencedaily.com/releases/1998/02/980204071837.htm (3 pages).

Arbiser, et al. Solenopsin, the alkaloidal component of the fire ant (*Solenopsis invicta*), is a naturally occurring inhibitor of phosphatidylinositol-3-kinase signaling and angiogenesis. Blood. 2007, 109(2):560-565.

Arendt, T. Alzheimer's disease as a loss of differentiation control in a subset of neurons that retain immature features in the adult brain. Neurobiol. Aging. 2000, 21(6):783-796.

Beak, et al. α-Lithiomine Synthetic Equivalents: Syntheses of Diastereoisomers from Boc Derivatives of Cycle Amines. J. Org. Chem. 1993, 58:1109-1117.

Borroni, et al. Amyloid precursor protein in platelets of patients with Alzheimer disease: effect of acetylcholinesterase inhibitor treatment. Arch. Neurol. 2001, 58(3):442-446.

Buell, et al. Dendritic growth in the aged human brain and failure of growth in senile dementia. Science. 1979, 206(4420):854-856.

Cheetham, et al. Isolation of single immunohistochemically identified whole neuronal cell bodies from post-mortem human brain for simultaneous analysis of multiple gene expression. J. Neurosci. Methods. 1997, 77(1):43-48.

Chow, et al. Expression profiles of multiple genes in single neurons of Alzheimer's disease. Proc. Natl. Acad. Sci. USA. 1998, 95 9620-9625.

Coleman, et al. Neuron numbers and dendritic extent in normal aging and Alzheimer's disease. Neurobiol. Aging. 1987, 8(6):521-545.

Comins, et al. Stereocontrolled preparation of cis- and trans-2,6-dialkylpiperidines via 1-acyldihydropyridine intermediates. Synthesis of (+)-solenopsin A and (+)-dihydropinidine. J. Org. Chem. 1991, 56:2506-2512.

Deslippe, et al. Venom alkaloids of fire ants in relation to worker size and age. Toxicon. 2000, 38(2): 223-232.

Doebler, et al. Neuronal RNA in Relation to Neuronal Loss and Neurofibrillary Pathology in the Hippocampus in Alzheimer's Disease. J. Neuropath Exp. Neurol. 1987, 46(1):28-39.

(Continued)

*Primary Examiner* — San-Ming Hui
(74) *Attorney, Agent, or Firm* — Ballard Spahr LLP

(57) ABSTRACT

Provided herein are piperidine alkaloids and uses thereof in neurological disorders and physical enhancement applications.

8 Claims, 6 Drawing Sheets

(56) References Cited

OTHER PUBLICATIONS

Felpin, et al. Recent Developments in the Synthesis of chiral 2,6-Dialkyl-1,2,5,6-Tetrahydropyridines and their Applications in Total Synthesis. Curr. Org. Synth. 2004, 1:83-109.
Flood, et al. Age-related dendritic growth in dentate gyrus of human brain is followed by regression in the "oldest old." Brain Res. 1985, 345(2):366-368.
Flood et al. Dendritic extent in human dentate gyrus granule cells in normal aging and senile dementia. Brain Res. 1987, 402(2): 205-216.
Folstein, et al. "Mini-mental state". A practical method for grading the cognitive state of patients for the clinician. J. Psychiatr. Res. 1975, 12(3):189-198.
Francis, et al. aph-1 and pen-2 Are Required for Notch Pathway Signaling, gamma-Secretase Cleavage of betaAPP, and Presenilin Protein Accumulation. Dev. Cell. 2002, 3(1):85-97.
Gearing, et al. The Consortium to Establish a Registry for Alzheimer's Disease (CERAD). Part X. Neuropathology confirmation of the clinical diagnosis of Alzheimer's disease. Neurology. 1995, 45(3 Pt 1):461-466.
Ginsberg, et al. Expression profile of transcripts in Alzheimer's disease tangle-bearing CA1 neurons. Annals of Neurology. 2000, 48(1):77-87.
Griffin, et al. Polyadenylated Messenger RNA in Paired Helical Filament-Immunoreactive Neurons in Alzheimer Disease. Alzheimer Disease & Associated Disorders. 1990, 4(2):69-78.
Haass, et al. The presenilins in Alzheimer's disease—proteolysis holds the key. Science. 1999, 286:916-919.
Harrison, et al. Regional and neuronal reductions of polyadenylated messenger RNA in Alzheimer's disease. Psychological Medicine. 1991, 21:855-866.
Haugabook, et al. Reduction of Aβ accumulation in the Tg2576 animal model of Alzheimer's disease after oral administration of the phosphatidyl-inositol kinase inhibitor wortmannin. The FASEB Journal. 2001, 15:16-18.
Howell, et al. Cardiodepressant and neurologic actions of *Solenopsis invicta* (imported fire ant) venom alkaloids. Ann. Allergy Asthma Immunol. 2005, 94(3):380-386.
Husseman, et al. Mitotic activation: a convergent mechanism for a cohort of neurodegenerative diseases. Neurobiology of Aging. 2000, 21(6):815-528.
Iwatsubo, et al. Visualization of A beta 42(43) and A beta 40 in senile plaques with end-specific A beta monoclonals: evidence that an initially deposited species is A beta 42(43). Neuron. 1994, 13(1):45-53.
Jouvenaz, et al. Antibacterial Activity of Venom Alkaloids from the Imported Fire Ant, *Solenopsis invicta* Buren. Antimicrob. Agents Chemother. 1972, 2(4):291-293.
Jung, et al. β-Amyloid precursor protein is detectable on monocytes and is increased in Alzheimer's disease. Neurobiology of Aging. 1999, 20(3):249-257.
Li, et al. SEL-10 interacts with presenilin 1, facilitates its ubiquitination, and alters A-beta peptide production. J. Neurochem. 2002, 82(6):1540-1548.
Mann, et al. Predominant deposition of amyloid-beta 42(43) in plaques in cases of Alzheimer's disease and hereditary cerebral hemorrhage associated with mutations in the amyloid precursor protein gene. Am. J. Pathol. 1996, 148(4): 1257-1266.
Monfray, et al. A new asymmetric synthesis of 2,6-cis-disubstituted 4-methylenepiperidines: total synthesis of (+)-alkaloid 241D and (+)- isosolenopsin A. Tetrahedrom: Asymmetry. 2005, 16(5):1025-1034.
Nagy, et al. Cell cycle regulatory failure in neurones: causes and consequences. Neurobiology of Aging. 2000, 21(6):761-769.
Peters, R. Tetraponerine-8, Ant Alkaloid: Pesticide or medicine. The Preliminary Program for 38th Middle Atlantic regional Meeting. Jun. 4-7, 2006. Poster.
Roher, et al. β-Amyloid-(1-42) is a major component of cerebrovascular amyloid deposits: Implications for the pathology of Alzheimer disease. Proc. Natl. Acad. Sci. USA. 1993, 90:10836-10840.

Rosen, et al. A new rating scale for Alzheimer's disease. Am. J. Psychiatry. 1984, 141:1356-1364.
Saunders, et al. BACE Maps to Chromosome 11 and a BACE Homolog, BACE2, Reside in the Obligate Down Syndrome Region of Chromosome 21. Science. 1999, 286:1255a.
Scheff, et al. Quantitative assessment of cortical synaptic density in Alzheimer's disease. Neurobiol. Aging. 1990, 11(1):29-37.
Schmitz, et al. The biological role of the Alzheimer amyloid precursor protein in epithelial cells. Histochem. Cell Biol. 2002, 117(2):171-180.
Selkoe, et al. Translating cell biology into therapeutic advances in Alzheimer's . disease. Nature. 1999, 399:A23-A31.
Solley, et al. Anaphylaxis due to Red Imported Fire Ant sting. MJA. 2002, 176:521-523.
Steiner, et al. PEN-2 Is an Integral Component of the γ-Secretase Complex Required for Coordinated Expression of Presenilin and Nicastrin. J. Biol. Chemistry. 2002, 277(42):39062-39065.
Strittmatter, et al. Apolipoprotein E: high-avidity binding to beta-amyloid and increased frequency of type 4 allele in late-onset familial Alzheimer disease. Proc Natl Acad Sci USA. 1993, 90(5):1977-1981.
Takahata, et al. A new route to trans-2,6-disubstituted piperdine-related alkaloids using a novel C2-symmetric 2,6-diallylpiperidine carboxylic acid methyl ester. Org. Biomol. Chem. 2006, 4(8):1587-1595.
Terry, et al. Neocortical cell counts in normal human adult aging. Ann. Neurol. 1987, 21:530-539.
Unger. Glial reaction in aging and Alzheimer's disease. Microsc Res Tech. 1998, 43(1):24-28.
Vassar, et al. β-Secretase Cleavage of Alzheimer's Amyloid Precursor Protein by the Transmembrane Aspartic Protease BACE. Science. 1999, 286(5440):735-741.
Vincent, et al. Aberrant Expression of Mitotic Cdc2/Cyclin B1 Kinase in Degenerating Neurons of Alzheimer's Disease Brain. J. Neurosci. 1997, 17:3588-3598.
Wakutani, et al. Heat Shock Protein 70 mRNA Levels in Mononuclear Blood Cells from Patients with Dementia of the Alzheimer Type. Dement Geriatr Cogn Disord. 1995, 6(6):301-305.
Wang, et al. Nonracemic Betti Base as a New Chiral Auxiliary: Application to Total Syntheses of Enantiopure (2S,6R)-Dihydropinidine and (2S, 6R)-Isosolenopsins. J. Org. Chem. 2005, 70:1897-1900.
Wilkinson, et al. Enantioselective Syntheses of 2-Alkyl- and 2,6-Dialkylpiperidine Alkaloids: Preparations of the Hydrochlorides of (−)-Coniine, (−)-Solenopsin A, and (−)-Dihydropinidine. Org. Let. 2000, 2(2):155-158.
West, et al. Differences in the pattern of hippocampal neuronal loss in normal aging and Alzheimer's disease. Lancet. 1994, 344:769-772.
Wolfe, et al. Peptidomimetic Probes and Molecular Modeling Suggest that Alzheimer's γ-Secretase Is an Intramembrane-Cleaving Aspartyl Protease. Biochemistry. 1999, 38:4720-4727.
Yamaguchi, et al. Immunohistochemical analysis of COOH-termini of amyloid beta protein (Aβ) using end-specific antisera for Aβ40 and Aβ42 in Alzheimer's disease and normal aging. Amyloid Int. J. Clin. Invest. 1995, 2(1):7-16.
Yamauchi, et al. Syntheses of (+)-and (−)-dihydopinidine and (−)-and (−)-epidihydropinidine by using yeast reduction of methyl (2-oxocyohexyl)acetate. Biosci. Biotechnol. Biochem. 2004, 68(3):676-684.
Yao, et al. Reduction of O-Linked N-Acetylglucosamine-Modified Assembly Protein-3 in Alzheimer's Disease. J. Neurosci. 1998, 18(7):2399-2411.
Yi, et al. Fire ant venom alkaloid, isosolenopsin A, a potent and selective oxide synthase. Int. J. Toxicol. 2003, 22(2):81-86.
Zhang, et al. Characterization of β-amyloid peptide precursor processing by the yeast Yap3 and Mkc7 proteases. Biochim. Biophys. Acta. 1997, 1359:110-122.
Notice of Acceptance issued Jul. 16, 2013 for Australian Application No. 2007272619, which claims priority to PCT/US2007/073018 filed on Jul. 9, 2007. (Applicant—Synapsin Pharmaceuticals, Inc. // Inventors—Dorsey et al.) (2 pages).
Response to Examination Report filed Jun. 13, 2013 for Australian Application No. 2007272619, which claims priority to PCT/US2007/

(56) References Cited

OTHER PUBLICATIONS 073018 filed on Jul. 9, 2007. (Applicant—Synapsin Pharmaceuticals, Inc. // Inventors—Dorsey et al.) (17 pages).
First Examination Report issued Feb. 14, 2012 for Australian Application No. 2007272619, which claims priority to PCT/US2007/073018 filed on Jul. 9, 2007. (Applicant—Synapsin Pharmaceuticals, Inc. // Inventors—Dorsey et al.) (2 pages).
Response to Official Action filed Nov. 25, 2013 Canadian Patent Application 2,657,256, which claims priority to PCT/US2007/073018 filed on Jul. 9, 2007. (Applicant—Synapsin Pharmaceuticals, Inc. // Inventors—Dorsey et al.) (22 pages).
Notice of Reinstatement issued Aug. 9, 2013 Canadian Patent Application 2,657,256, which claims priority to PCT/US2007/073018 filed on Jul. 9, 2007. (Applicant—Synapsin Pharmaceuticals, Inc. // Inventors—Dorsey et al.) (1 page).
Notice of Abandonment issued Aug. 9, 2013 Canadian Patent Application 2,657,256, which claims priority to PCT/US2007/073018 filed on Jul. 9, 2007. (Applicant—Synapsin Pharmaceuticals, Inc. // Inventors—Dorsey et al.) (1 page).
Office Action issued May 23, 2013 for Canadian Patent Application 2,657,256, which claims priority to PCT/US2007/073018 filed on Jul. 9, 2007. (Applicant—Synapsin Pharmaceuticals, Inc. // Inventors—Dorsey et al.) (3 pages).
Amendment filed on Aug. 31, 2009 for Canadian Patent Application 2,657,256, which claims priority to PCT/US2007/073018 filed on Jul. 9, 2007. (Applicant—Synapsin Pharmaceuticals, Inc. // Inventors—Dorsey et al.) (3 pages).
Amended claims filed in Response to Notification of Reexamination filed Apr. 25, 2014 for Chinese Patent Application No. 200780033059.9, which claims priority to PCT/US2007/073018 filed on Jul. 9, 2007. (Applicant—Synapsin Pharmaceuticals, Inc. // Inventors—Dorsey et al.) (1 page).
Decision on Rejection issued on May 3, 2012 for Chinese Patent Application No. 200780033059.9, which claims priority to PCT/US2007/073018 filed on Jul. 9, 2007. (Applicant—Synapsin Pharmaceuticals, Inc. // Inventors—Dorsey et al.) (7 pages).
First Office Action issued on Oct. 13, 2010 for Chinese patent Application No. 200780033059.9, which claims priority to PCT/US2007/073018 filed on Jul. 9, 2007. (Applicant—Synapsin Pharmaceuticals, Inc. // Inventors—Dorsey et al.) (6 pages).
Examination Report issued on May 9, 2014 for European Patent Application No. 07812708.1, which claims priority to PCT/US2007/073018 filed on Jul. 9, 2007. (Applicant—Synapsin Pharmaceuticals, Inc. // Inventors—Dorsey et al.) (5 pages).
Response to Examination Report filed on Dec. 19, 2011 for European Patent Application No. 07812708.1, which claims priority to PCT/US2007/073018 filed on Jul. 9, 2007. (Applicant—Synapsin Pharmaceuticals, Inc. // Inventors—Dorsey et al.) (7 pages).
Article 94(3) EPC Communication issued on Aug. 8, 2011 for European Patent Application No. 07812708.1, which claims priority to PCT/US2007/073018 filed on 07/09/07. (Applicant—Synapsin Pharmaceuticals, Inc. // Inventors—Dorsey et al.) (5 pages).
European Search Report issued on Jul. 12, 2010 for European patent Application No. 07812708.1, which claims priority to PCT/US2007/073018 filed on Jul. 9, 2007. (Applicant—Synapsin Pharmaceuticals, Inc. // Inventors—Dorsey et al.) (8 pages).
Notice of Allowance issued Jan. 22, 2014 for Japanese Application No. 2009-519616, which claims priority to PCT/US2007/073018 filed on Jul. 9, 2007. (Applicant—Synapsin Pharmaceuticals, Inc. // Inventors—Dorsey et al.) (3 pages).
Amended Claims filed on Dec. 16, 2013 for Japanese Application No. 2009-519616, which claims priority to PCT/US2007/073018 filed on Jul. 9, 2007. (Applicant—Synapsin Pharmaceuticals, Inc. // Inventors—Dorsey et al.) (3 pages).
Amended Claims filed on Jul. 25, 2013 for Japanese Application No. 2009-519616, which claims priority to PCT/US2007/073018 filed on Jul. 9, 2007. (Applicant—Synapsin Pharmaceuticals, Inc. // Inventors—Dorsey et al.) (3 pages).
Final Office Action issued Mar. 27, 2013 for Japanese Patent Application 2009-519616, which claims priority to PCT/US2007/073018 filed on Jul. 9, 2007. (Applicant—Synapsin Pharmaceuticals, Inc. // Inventors—Dorsey et al.) (6 pages).
Amended Claims filed on Feb. 7, 2013 for Japanese Application No. 2009-519616, which claims priority to PCT/US2007/073018 filed on Jul. 9, 2007. (Applicant—Synapsin Pharmaceuticals, Inc. // Inventors—Dorsey et al.) (3 pages).
Office Action issued Sep. 6, 2012 for Japanese Application No. 2009-519616, which claims priority to PCT/US2007/073018 filed on Jul. 9, 2007. (Applicant—Synapsin Pharmaceuticals, Inc. // Inventors—Dorsey et al.) (12 pages).
Amended Claims filed on Mar. 11, 2009 for Japanese Application No. 2009-519616, which claims priority to PCT/US2007/073018 filed on Jul. 9, 2007. (Applicant—Synapsin Pharmaceuticals, Inc.//Inventors—Dorsey et al.) (3 pages).
International Preliminary Report on Patentability issued on Jan. 13, 2009 for PCT/US2007/073018 filed on Jul. 9, 2007 and published as WO 2008/008720 on Jan. 17, 2008 (Applicant—Synapsin Pharmaceuticals, Inc. // Inventors—Dorsey et al.) (4 pages).
International Search Report and Written Opinion issued on Aug. 7, 2008 for PCT/US2007/073018 filed on Jul. 9, 2007 and published as WO 2008/008720 on Jan. 17, 2008 (Applicant—Synapsin Pharmaceuticals, Inc. // Inventors—Dorsey et al.) (5 pages).
Issue Notification issued Aug. 14, 2013 for U.S. Appl. No. 12/307,459, filed Nov. 2, 2009 (Inventors—Dorsey et al.) (1 page).
Notice of Allowance and Fee(s) Due issued Jul. 19, 2012 for U.S. Appl. No. 12/307,459, filed Nov. 2, 2009 (Inventors—Dorsey et al.) (8 pages).
Response to Non-Final Office Action filed Apr. 16, 2013 for U.S. Appl. No. 12/307,459, filed Nov. 2, 2009 (Inventors—Dorsey et al.) (12 pages).
Non-Final Office Action issued Jan. 18, 2013 for U.S. Appl. No. 12/307,459, filed Nov. 2, 2009 (Inventors—Dorsey et al.) (9 pages).
Response to Restriction Requirement filed Nov. 8, 2012 for U.S. Appl. No. 12/307,459, filed Nov. 2, 2009 (Inventors—Dorsey et al.) (4 pages.).
Restriction Requirement issued Jun. 8, 2012 for U.S. Appl. No. 12/307,459, filed Nov. 2, 2009 (Inventors—Dorsey et al.) (6 pages).
Preliminary Amendment filed Oct. 29, 2009 for U.S. Appl. No. 12/307,459 filed Nov. 2, 2009 (Inventors—Dorsey et al.) (4 pages).

COMPOSITIONS AND METHODS RELATING TO SOLENOPSINS AND THEIR USES IN TREATING NEUROLOGICAL DISORDERS AND ENHANCING PHYSICAL PERFORMANCE

CROSS-REFERENCE TO RELATED APPLICATIONS

This application is a continuation-in-part of U.S. application Ser. No. 12/307,459, which is the National Stage of International Application No. PCT/US2007/073018, filed Jul. 9, 2007, which claims benefit of U.S. Provisional Application No. 60/806,887, filed Jul. 10, 2006, each of which is incorporated herein by reference in its entirety.

BACKGROUND OF THE INVENTION

A number of diseases and disorders involving the central nervous system are known, such as, for example, stroke and related ischemic diseases, spinal cord injuries, peripheral nerve injuries, traumatic brain injuries, retinal degeneration, epilepsy (such as generalized, partial, or refractory epilepsy), neuropsychiatric disorders, pain disorders and neurodegenerative disorders. Alzheimer's disease (AD) is most commonly associated with deposition of amyloid-$\beta$ (A$\beta$) peptide in the brain. Oxidative stress and inflammation are important pathogenic mechanisms of Alzheimer's disease (AD) and related disorders. The presence of A$\beta$ peptide in the brain plays an important role in the development of aggregates that may result in neuronal damage and dysfunction and microglial activation and neuropathological features of AD. A$\beta$ (with or without tau/neurofibrillary tangles (NFTs)) perturbs cellular properties mainly by oxidant stress and inflammation, which overwhelms the cellular antioxidant/anti-inflammatory defense-mechanisms. Currently, the only available treatments for AD are acetylcholinesterase inhibitors which have limited capabilities of reducing the effects of AD. However, current data suggests that the acetylcholinesterase inhibitors accelerate the process of AD. Therefore, it is crucial for the development of new therapeutics to treat the disease for AD as well as other neurological diseases and disorders.

BRIEF SUMMARY OF THE INVENTION

In accordance with the purpose of this invention, as embodied and broadly described herein, this invention relates to piperidine alkaloids and uses thereof in neurological applications.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

DETAILED DESCRIPTION OF THE INVENTION

Figure 1:
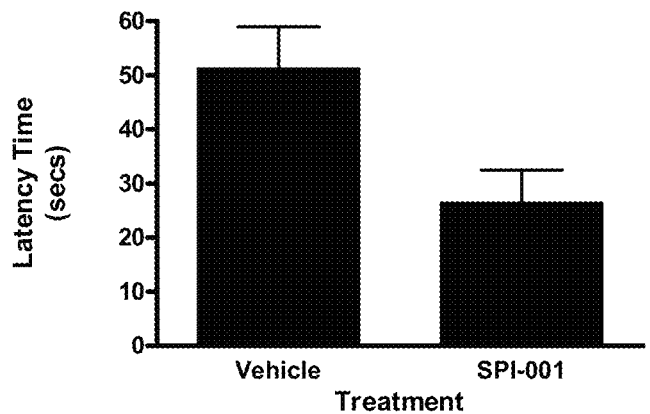
FIG. 1 shows behavioral changes in APP mice chronically treated with SPI-001 at 10 mg/kg/day for 90 days. Morris water maze test.

The disclosed method and compositions may be understood more readily by reference to the following detailed description of particular embodiments and the Example included therein and to the Figures and their previous and following description.

It has been discovered that piperidine alkaloids, such as Solenopsin A, found in fire ant venom, can be used to treat and/or prevent, for example, neurological disease or dysfunction or for the enhancement of neurological or cognitive function. Other uses are disclosed, apparent from the disclosure, and/or will be understood by those in the art.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an alkaloid is disclosed and discussed and a number of modifications that can be made to a number of molecules including the alkaloid are discussed, each and every combination and permutation of alkaloid and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. DEFINITIONS

It must be noted that as used herein and in the appended claims, the singular forms "a," "an," and "the" include plural reference unless the context clearly dictates otherwise. Thus, for example, reference to "an alkaloid" includes a plurality of such alkaloids, reference to "the alkaloid" is a reference to one or more alkaloids and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

As used herein, "subject" can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. The term "patient" refers to a subject afflicted with a disease or disorder includes human and veterinary subjects.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutically effective" means that the amount of the composition used is of sufficient quantity to ameliorate one or more causes or symptoms of a disease or disorder. Such amelioration only requires a reduction or alteration, not necessarily elimination. As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 30 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. The term alkyl also includes "cycloalkyl," which is a cyclic alkyl group such as cyclobutyl, cyclopentyl, cyclohexyl, cycloheptyl, and the like.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 30 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. The term alkenyl also includes "cycloalkenyl," which is a cyclic alkenyl group such as cyclobutenyl, cyclopentenyl, cyclohexenyl, cycloheptenyl, and the like.

The term "alkynyl" as used herein is a hydrocarbon group of 2 to 30 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. The term alkyl also includes "cycloalkynyl," which is a cyclic alkyl group such as cyclobutynyl, cyclopentynyl, cyclohexynyl, cycloheptynyl, and the like.

The term "aliphatic" is used herein to refer to an alkyl, alkenyl, or alkynyl group as defined herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O—.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "silyl" as used herein is represented by the formula $—SiA^1A^2A^3$, where $A^1$, $A^2$, and $A^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. Throughout this specification "S(O)" is a short hand notation for S=O The term "sulfonyl" is used herein to refer to the sulfo-oxo group represented by the formula $—S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH—$.

The term "sulfone" as used herein is represented by the formula $A^1S(O)_2A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" as used herein is represented by the formula $A^1S(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

"$R^1$," "$R^2$," "$R^3$," "$Rn$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

B. COMPOSITIONS

Provided herein are piperidine alkaloids and uses thereof in neurological applications. These piperidine alkaloids can be derived from venom, such as fire ant venom, or they can be synthesized as disclosed herein.

1. Fire Ant Venom

Solenopsins are piperidine alkaloids derived from the venom of the red fire ant *Solenopsis invicta*. The term "fire ant" and "*Solenopsis invicta*" are used interchangably to describe the common red fire ant, originating in South America, but now commonly found in 11 southeastern states of the United States, parts of the southwestern United States, California, and Puerto Rico. The term fire ant may also be used to describe black fire ants and other hybrid fire ants or other ants which produce solenopsin venom.

The venom of this insect consists of 95% alkaloids and the remainder contains solubilized proteins, amino acids and enzymes including hyaluronidase and phospholipase. Among the piperidine alkaloids in the venom, the two major components are Solenopsin A, a trans-2-methyl 6-n-undecylpiperidine and Solenopsin B, a 2,6-trans-dialkyl-piperidine.

The use of solenopsins for the elimination of ticks, fleas or other parasitic infections in dogs and cats has been disclosed by Rehmert et al. in U.S. Pat. Nos. 4,910,209, 5,075,320, and 5,098,914, which are hereby incorporated by reference herein in their entirety for these teachings. In this approach, the solenopsins were administered from the whole body extract of the insect or from an oral dosage form containing more highly purified material. The administration of these drugs over a period of one to eleven days with regular booster dosages disseminates the alkaloid composition through the blood and tissue fluids of the treated animals and eliminates fluid-feeding parasites.

2. Piperidine Alkaloids

Piperidine alkaloids can be used in the disclosed compositions and methods. Piperidine alkaloids, such as Solenopsin A, can also be synthetically produced. Unlike the whole body extract, it does not require refrigeration. However, higher numbers of units of the synthetic version are required for effective treatment. For example, 1,500 units of synthetically produced Solenopsin A are equivalent to 250 units of the whole body extracts.

The stings of Red Imported Fire Ants (*Solenopsis invicta* Buren) contain high alkaloid content in the venom, which exhibits potent necrotoxic activity. The major components of the venom have various cis and trans isomers of 2-methyl-6-n-alkyl piperidines, with the trans isomer predominating.

The chemical structures of the piperidine alkaloid, Solenopsin A, are shown below.

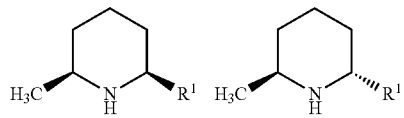

wherein $R^1$ is a C11 alkyl group (i.e., undecyl group). However, other compounds that can be present in venom in varying amounts, and are also suitable for the uses and compositions disclosed herein, include, but are not limited to, I. cis-2-methyl-6-undecylpiperidine
II. trans-2-methyl-6-undecylpiperidine
III. cis-2-methyl-6-tridecylpiperidine
IV. trans-2-methyl-6-tridecylpiperidine
V. cis-2-methyl-6-pentadecylpiperidine
VI. trans-2-methyl-6-pentadecylpiperidine
VII. cis-2-methyl-6-(cis-4-tridecen-1-yl)piperidine
VIII. trans-2-methyl-6-(cis-4-tridecen-1-yl)piperidine
IX. cis-2-methyl-6-(cis-4-pentadecen-1-yl)piperidine
X. trans-2-methyl-6-(cis-4-pentadecen-1-yl)piperidine Other examples of piperidine alkaloids that can be used in the disclosed compositions and methods can have the following general formula.

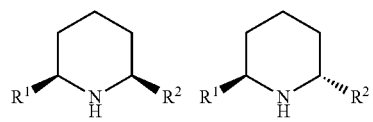

wherein $R^1$ is a short chain (i.e., 1-6 carbon atoms) substituted or unsubstituted aliphatic group, and $R^2$ is a long chain substituted or unsubstituted aliphatic group having from 7 to 30 carbon atoms. In many specific examples, $R^1$ is methyl, ethyl, or propyl, and $R^2$ is a alkyl or alkenyl group having from 10 to 20 carbons (i.e., 10, 11, 12, 13, 14, 15, 16, 17, 18, 19, or 20 carbons, including mixtures thereof).

Also contemplated herein are pharmaceutically acceptable salts of the disclosed piperidine alkaloids. Such salts can be prepared by treating the piperidine alkaloids with an appropriate amount of a pharmaceutically acceptable acid such as, for example, HCl, $H_2SO_4$, or $H_3PO_4$, to produce the cationic salt. In one example, the compound can be protonated with tartaric acid or acetic acid to produce the tartarate or acetate salt, respectively. In another example, the reaction of the compound with the acid is conducted in water, alone or in combination with an inert, water-miscible organic solvent, at a temperature of from about 0° C. to about 100° C., such as at room temperature. In certain situations, where applicable, the molar ratio of the disclosed compounds to base is chosen to provide the ratio desired for any particular salts.

3. Combinations

The methods and compositions disclosed herein can be used in combination with various compositions. For example, the following drugs and classes of drugs can be used for treatment of neurological disorders: opioids and opioid peptides, morphine, hydroxymorphine, fentanyl, oxycodone, codeine; capsaicin; as well as antiepileptic drugs as a class including but not limited to carbamazepine, primidone, gabapentin, pregabalin, diazepam, felbamate, fluorofelbamate, lamotrigine, lacosamide, levetiracetam, phenobarbital, phenyloin, fos-phenyloin, topiramate, valproate, vigabatrin, zonisamide, oxcarbazepine, nonsteroidal anti-inflammatory drugs (NSAIDs), local anesthetics (such as lidocaine), glutamate receptor antagonists, NMDA antagonists, alpha-adrenoceptor agonists and antagonists, adenosine, cannabinoids, NK-1 antagonist (CI-1021), antidepressants (amitriptyline, desipramine, imipramine, for example), analogs and derivatives of galanin, somatostatin, delta-sleep inducing peptide, enkephalins, oxytocin. cholecystikinin, calcitonin, cortistatin, nociceptin and other neuropeptide-based therapeutics, and pluronic P85 block copolymer.

4. Pharmaceutical Compositions

The present compounds or their derivatives, including pro-drug forms of these agents, can be provided in the form of pharmaceutically acceptable salts. As used herein, the term pharmaceutically acceptable salts or complexes refers to appropriate salts or complexes of the active compounds as disclosed herein which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, magnesium, manganese and the like, among numerous others, many of which may increase the water solubility of the compounds in final pharmaceutical dosage form.

Modifications of the active compound can affect the solubility, bioavailability and rate of metabolism of the active species, thus providing control over the delivery of the active species. The term "water soluble salt form" or "salt form" is used to describe forms of compounds as disclosed herein which are in their water soluble salt form. Salt forms of compounds as disclosed herein include any salt which retains the desired biological effects. Nonlimiting examples of such salts are acid addition salts formed with inorganic acids such as hydrochloric acid, hydrobromic acid, sulfuric acid, phosphoric acid, nitric acid and the like, salts formed with organic acids such as acetic acid, oxalic acid, tartaric acid, succinic acid, malic acid, ascorbic acid, benzoic acid, tannic acid, pamoic acid, alginic acid, glutamic acid, naphthalenesulfonic acids, naphthalenedisulfonic aicds and glacturonic acid, among numerous others. Salts may be formed by neutralizing the nitrogen on the piperidine ring with the resulting salts exhibiting substantially greater solubility or derliverability of the instant compounds. These may also affect the bioavailability and rate of metabolism or stability of the compounds as disclosed herein.

The disclosed compositions can be used therapeutically in combination with a pharmaceutically acceptable carrier. Thus, a piperidine alkaloids disclosed herein can be formulated in admixture with a pharmaceutically acceptable carrier, excipient or additive. By "pharmaceutically acceptable" is meant a material that is not biologically or otherwise undesirable, i.e., the material may be administered to a subject, along with the disclosed piperidines, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

C. METHODS

As disclosed herein, piperidine alkaloids can be used for the treatment of neurological disease or dysfunction or for the enhancement of neurological or cognitive function. Other uses are disclosed, apparent from the disclosure, and/or will be understood by those in the art.

Without wishing to be bound by theory, Solenopsin can, in some aspects, have its effect on neurological or cognitive function by inhibiting phosphatidylinositol-3-kinase (PBK) signaling. Beta secretase (BACE) expression results in increased intracellular AP 40-42 levels through the processing of amyloid precursor protein (APP). Thus, the herein disclosed piperidine alkaloids can be used in combinations with other PBK inhibitors. In addition, treatment of a subject with the disclosed piperidine alkaloids can be monitored by detecting PBK activity in target cells of the subject. This in turn can reduce APP processing in the cell such as through the APP rocessing can limit the production of Af3 peptides (1-40 and 1-42) and curb the extent of Alzheimer's disease (AD).

1. Neurological Disease

The methods and compositions disclosed herein can also be used in the prevention, amelioration, or treatment of a variety of diseases and disorders involving the central nervous system, such as, for example, stroke and related ischemic diseases, spinal cord injuries, peripheral nerve injuries, traumatic brain injuries, retinal degeneration, epilepsy (such as generalized, partial, or refractory epilepsy), neuropsychiatric disorders, and neurodegenerative disorders.

Neuropsychiatric disorders include, but are not limited to, schizophrenia, schizoaffective disorder, attention deficit disorder, dysthymic disorder, major depressive disorder, mania, obsessive-compulsive disorder, psychoactive substance use disorders, anxiety, panic disorder, as well as bipolar affective disorder, e.g., severe bipolar affective (mood) disorder (BP-I), bipolar affective (mood) disorder with hypomania and major depression (BP-II). Further CNS-related disorders include, for example, those listed in the American Psychiatric Association's Diagnostic and Statistical manual of Mental Disorders (DSM), the most current version of which is incorporated herein by reference in its entirety.

Non-limiting examples of neurodegenerative disorders include Alexander disease, Alper's disease, Alzheimer disease, Amyotrophic Lateral Sclerosis (ALS, Lou Gehrig's disease), Ataxia telangiectasia, Batten disease (also known as Spielmeyer-Vogt-Sjogren-Batten disease), Canavan disease, Cockayne syndrome, Corticobasal degeneration, Creutzfeldt-Jakob disease, Huntington disease, Kennedy's disease, Krabbe disease, Lewy body dementia, Machado-Joseph disease, Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spielmeyer-Vogt-Sjogren-Batten disease (also known as Batten disease), Spinocerebellar ataxia (multiple types with varying characteristics), Spinal muscular atrophy, Steele-Richardson-Olszewski disease, and Tabes dorsalis.

Alzheimer's disease is a progressive neurodegenerative disorder that is characterized by the formation of senile plaques and neurofibrillary tangles containing amyloid β (Aβ) peptide. These plaques are found in limbic and association cortices of the brain. The hippocampus is part of the limbic system and plays an important role in learning and memory. In subjects with Alzheimer's disease, accumulating plaques damage the neuronal architecture in limbic areas and eventually cripple the memory process.

Approximately twenty million people worldwide suffer with dementia that results from Alzheimer's disease. The disease can be early onset affecting individuals as young as 30 years of age, or it can be familial or sporadic. Familial Alzheimer's disease was once thought to be inherited strictly as an autosomal dominant trait; however, this view is changing as more genetic determinants are isolated. For example, some normal allelic variants of apolipoprotein E (ApoE), which is found in senile plaques, can either protect against or increase the risk of developing the disease (Strittmatter et al. (1993) Proc Natl Acad Sci 90:1977-1981).

Amyloid-β (Aβ) peptides are metabolites of the Alzheimer's disease-associated precursor protein, β-amyloid precursor protein (APP), and are believed to be the major pathological determinants of Alzheimer's disease (AD). These peptides consist mainly of 40 to 42 amino acids, Aβ1-40 ("Aβ40") and Aβ1-42 ("Aβ42"), respectively. Aβ40 and Aβ42 are generated by two enzymatic cleavages occurring close to the C-terminus of APP. The enzymes responsible for the cleavage, β-secretase and γ-secretase, generate the – and C-termini of Aβ, respectively. The amino terminus of Aβ is formed by β-secretase cleavage between methionine residue 596 and aspartate residue 597 of APP (APP 695 isoform numbering) (see, e.g., U.S. Pat. No. 6,440,698; and U.S. Pat. No. 5,744,346).

γ-secretase activity cleaves at varying positions 38-, 40- or 43-residues C-terminal of this β-secretase cleavage to release Aβ peptides (see, e.g., U.S. Patent Application 20020025540). The complete molecular identity of γ-secretase enzyme is still unknown. Presenilin 1, or the closely related presenilin 2, is needed for γ-secretase activity. γ-secretase activity is reduced 80% in cultured cells derived from embryos genetically deleted for presenilin 1. All γ-secretase activity is lost in cells lacking both presenilin 1 and presenilin 2. Peptidomimetic inhibitors of γ-secretase activity can be crosslinked to presenilins 1 and 2, suggesting that these proteins are catalytic subunits for the cleavage. However, γ-secretase activity isolated from cells chromatographs as a large complex>1 M daltons. Genetic studies have identified three more proteins required for γ-secretase activity; nicastrin, aph-1 and pen-1. (Francis et al., 2002, Developmental Cell 3(1): 85-97; Steiner et al., 2002, J. Biol. Chemistry: 277(42): 39062-39065; and Li et al., 2002, J. Neurochem. 82(6): 1540-1548). Accumulation of presenilin into high molecular weight complexes is altered in cells lacking these proteins.

A third enzyme, α-secretase, cleaves the precursor protein between the β- and γ-cleavage sites, thus precluding AP production and releasing an approximately 3 kDa peptide known as P3, which is non-pathological. Both β- and α-secretase cleavage also result in soluble, secreted—terminal fragments of APP, known as sAPβ and sAPPα, respectively. The sAPPα fragment has been suggested to be neuroprotective.

In normal individuals, the Aβ peptide is found in two predominant forms, the majority Aβ-40 (also known as Aβ1-40) form and the minority Aβ42 (also known as Aβ1-42) form, each having a distinct COOH-terminus. The major histological lesions of AD are neuritic plaques and neurofibrillary tangles occurring in affected brain regions. Neuritic plaques consist of Aβ peptides, primarily Aβ40 and Aβ42. Although healthy neurons produce at least ten times more Aβ40 compared to Aβ42, plaques contain a larger proportion of the less soluble Aβ42. Patients with the most common form of familial Alzheimer's disease show an increase in the amount of the Aβ42 form. The Aβ40 form is not associated with early deposits of amyloid plaques. In contrast, the Aβ42 form accumulates early and predominantly in the parenchymal plaques and there is strong evidence that Aβ42 plays a major role in amyloid plaque deposits in familial Alzheimer's disease patients (Roher et al., 1993, Proc. Natl. Acad. Sci. USA 90:10836; Iwatasubo, T., et al., 1994 Neuron 13:45; Yamaguchi et al, 1995, Amyloid Int. J. Clin. Invest. 2:7-16; and Mann et al., 1996 Am. J. Pathol. 148:1257).

Mutations in four genes are known to predispose an individual to Alzheimer's disease: ApoE, amyloid precursor protein (APP), presenilin-1, and presenilin-2 (Selkoe (1999) Nature 399:A23-A31). The e4 allele of the ApoE gene confers increased risk for late onset Alzheimer's disease. β-amyloid protein (Aβ) is the major component of senile plaques, and it is normally formed when β- and γ-secretase cleave APP. In Alzheimer's disease patients, large quantities of Aβ are generated and accumulate extracellularly in these neuropathological plaques. Efforts to understand the mechanism underlying Aβ deposition have recently focused on the APP-cleaving secretase. In fact, two yeast aspartyl proteases have been shown to process APP in vitro (Zhang et al. (1997) Biochem Biophys Acta 1359:110-122). Evidence using peptidomimetic probes further confirms that the secretase is an intramembrane-cleaving aspartyl protease (Wolfe et al. (1999) Biochemistry 38:4720-4727). The presenilin-1 gene is a candidate for the γ-secretase that cleaves the APP carboxyl terminus. Several lines of evidence support the involvement of presenilins in the disease process. Presenilin can be coimmunoprecipitated with APP, and mutations in the presenilin genes increase production of the 42-amino acid peptide form of Aβ. These missense point mutations result in a particularly aggressive, early onset form of the disease (Haaas and DeStrooper (1999) Science 286:916-919).

The proteases, BACE1 and BACE2 (β-site APP cleaving enzymes 1 and 2) which appear to be β-secretase, are potential therapeutic targets because of their ability to cleave APP. Vassar et al. (1999; Science 286:735-741) have found that BACE1 is an aspartyl protease with β-secretase activity which cleaves APP to produce Aβ peptide in vitro. It is expressed at moderate levels across all brain regions and is concentrated in neurons but not in glia. BACE2, which has 52% amino acid identity with BACE1, has been described by Saunders et al. (1999; Science 286:1255a). Whereas BACE1 maps to the long arm of chromosome 11, BACE2 maps to the Down syndrome region of chromosome 21 (Acquati et al. (2000) 468: 59-64; Saunders et al. supra). This location is significant because middle-aged Down syndrome patients have enhanced β-amyloid deposits. Other members of the BACE family can also participate in this APP cleavage: the amino terminals of Aβ peptides appear to be cleaved heterogeneously indicating that there can be several β-secretase involved in APP processing (Vassar (1999) Science 286:735-741).

Associations between Alzheimer's disease and many other genes and proteins have been reported. Fetal Alzheimer antigen (FALZ) and synuclein a (SNCA) are found in brain plaques and tangles. Inheritance of some gene polymorphisms is also linked to increased risk of developing the disease. For example, a polymorphism in the gene encoding β2-macroglobulin, a protein that can act as a protease inhibitor, is associated with increased risk for developing a late-onset form of Alzheimer's disease.

One hundred years ago Alois Alzheimer described the major behavioral and neuropathological features of the neurodegenerative disorder bearing his name. AD is characterized clinically/behaviorally by progressive impairment of memory and cognition. Neuropathological and neurobiological changes associated with this slow progression of clinical symptoms include accumulation of amyloid plaques and neurofibrillary tangles (NFTs) (Gearing M. et al., The Consortium to Establish a Registry for Alzheimer's Disease (CERAD). Part X. Neuropathology confirmation of the clinical diagnosis of Alzheimer's disease. Neurology. 1995; 45(3 Pt 1):461-466) gliosis (Unger J W., Microscopy Res. Technique. 1998; 43:24-28), reduced dendritic plasticity relative to normal aged (Buell S J. Coleman P D., Science. 1979; 206(4420):854-856), Flood D G. et al., Brain Research. 1985; 345(2):366-368, Flood D G., et al., Brain Research. 1987; 402(2):205-216), and reduced density of neurons (Coleman P D. Flood D G., et al., Neurobiology of Aging. 1987; 8(6):521-545), Terry R D, et al., 1987; 21:530-539, West M J, et al., Lancet. 1994; 344:769-772) and synapses (Scheff S W. et al., Neurobiology of Aging. 1990; 11(1):29-37).

Studies of altered gene expression in Alzheimer's disease brain tissue have shown a general reduction of message level estimated at about 35% (Doebler J A, et al., Journal of Neuropathology & Experimental Neurology. 1987; 46(1):28-39), (Griffin W S, et al., Alzheimer Disease & Associated Disorders. 1990; 4(2):69-78), (Harrison P J, et al., Psychological Medicine. 1991; 21:855-866). Against this background of a general reduction of mRNA, selected studies have demonstrated increased as well as decreased expression of a wide variety of genes. Some gene classes affected in Alzheimer's disease are expressed in a neuron specific manner. These especially include decreased expression of selected genes that are related to synaptic structure and function and the neuronal cytoskeleton (Ginsberg S D. et al., Annals of Neurology. 2000; 48(1):77-87), (Yao P, et al., Journal of Neuroscience. 1998; 18(7):2399-2411). Other classes of genes whose expression is altered in AD include those related to the cell cycle (Arendt T., Neurobiology of Aging. 2000; 21(6): 783-796), (Husseman J W., et al., Neurobiology of Aging. 2000; 21(6):815-828), (Nagy Z., et al., Neurobiology of Aging. 2000; 21(6):761-769), (Vincent I, et al., J. Neurosci. 1997; 17:3588-3598) and inflammatory/stress responses (for a review, see (Akiyama H., et al., Neurobiology of Aging. 2000; 21(3):383-421)). These gene classes are expressed in a variety of cell types that reside outside the nervous system including leukocytes (Wakutani Y. et al., Dementia. 1995; 6(6):301-305), monocytes (Jung S S. et al., Neurobiology of Aging. 1999; 20(3):249-257), and epithelial cells (Schmitz A., et al., Histochemistry & Cell Biology. 2002; 117(2):171-180) as well as other cell types.

Multivariate analysis of profiles of expression of multiple gene products (messages) by single neurons or homogenates from postmortem human brain can be used to distinguish Alzheimer's disease from control samples (Cheetham J E., et al., Journal of Neuroscience Methods. 1997; 77(1):43-48, Chow, N., et al., Proc. Natl. Acad. Sci. USA. 1998; 95:9620-9625).

Symptoms of Aβ-related disorders are well known to those of skill in the art. For example, symptoms of Alzheimer's disease are well known in the art and can include, e.g., memory loss, mild cognitive impairment, cognitive decline, severe cognitive impairment and personality changes that result in loss of functional ability, e.g., over the course of a decade. In debilitated states, patients usually exhibit severe impairment, and retain only vegetative neurologic function. Symptoms of Alzheimer's disease can also include certain art-known neuropathological lesions, including intracellular neurofibrillary tangles and extracellular parenchymal and cerebrovascular amyloid.

Thus, provided is a method of treating or preventing Alzheimer's disease in a subject comprising administering to the subject a therapeutically effective amount of a composition comprising a piperidine alkaloid. Also provided is a method of treating a subject at risk for Alzheimer's disease comprising administering to the subject a composition comprising a piperidine alkaloid. As used herein, the terms "disorder" and "disease" are used interchangeably to refer to a condition in a subject.

As used herein, the term "Aβ-related disorder" or an "Aβ disorder" is a disease (e.g., Alzheimer's disease) or a condition (e.g., senile dementia) that involves an aberration or dysregulation of Aβ levels. An Aβ-related disorder includes, but is not limited to Alzheimer's disease, Down's syndrome and inclusion body myositis. Thus, the Aβ related disorder can be Alzheimer's disease. The progression of the Aβ related disorder can be slowed or reversed. Also provided is a method for modulating amyloid-β peptide (Aβ) levels exhibited by a cell or tissue comprising contacting said cell or tissue with an amount of a composition comprising a piperidine alkaloid sufficient to modulate said Aβ levels.

As used herein, a cell or tissue may include, but not be limited to: an excitable cell, e.g., a sensory neuron, motorneuron, or interneuron; a glial cell; a primary culture of cells, e.g., a primary culture of neuronal or glial cells; cell(s) derived from a neuronal or glial cell line; dissociated cell(s); whole cell(s) or intact cell(s); permeabilized cell(s); a broken cell preparation; an isolated and/or purified cell preparation; a cellular extract or purified enzyme preparation; a tissue or organ, e.g., brain, brain structure, brain slice, spinal cord, spinal cord slice, central nervous system, peripheral nervous system, or nerve; tissue slices, and a whole animal. In certain embodiments, the brain structure is cerebral cortex, the hippocampus, or their anatomical and/or functional counterparts in other mammalian species. In certain embodiments, the cell or tissue is an N2a cell, a primary neuronal culture or a hippocampal tissue explant.

2. Enhance Neurological Function and Physical Performance

The methods and compositions disclosed herein can also be used in the enhancement of neurological and/or cognitive function. Cognitive enhancement may be defined for present purposes as a measurable improvement in a cognitive ability of a mammalian subject. Methods and means of measuring cognitive abilities of experimental laboratory animals, such as rats, are well-known to those skilled in the art (e.g., shuttle boxes, Morris-mazes, etc). Similarly, there are methods of measuring the cognitive abilities of human subjects (e.g., as employed by Becker et al) known to, those skilled in the art. A number of tests have been used to investigate the cognitive abilities of Alzheimer's Disease patients in clinical trials to assess the effectiveness of drug therapies. Examples include the "Alzheimer Disease Assessment Scale" (ADAS-Cog) (Rosen et al, Am. J. Psychiatry 1984 141, 1356-1364) and the "Mini Mental State Examination" (MMSE) (Rosen et al, J. Psychiatric Res. 1975 12, 189-198). Cognitive enhancement is detected by a statistically significant improvement (e.g. in the test group receiving the drug compared to a control group, as measured by an appropriate statistical test (e.g. Student's T test).

The methods and compositions disclosed herein can also be used in the enhancement of physical performance. Physical performance enhancement may be defined for present purposes as a measurable improvement in a physical ability of a mammalian subject. Methods and means of measuring physical abilities of experimental laboratory animals, such as rats, are well-known to those skilled in the art (e.g., grip strength, treadmill, etc). Similarly, there are methods of measuring the physical abilities of human subjects known to those skilled in the art. A number of tests have been used to investigate the physical abilities of individuals.

3. Method of Making

The disclosed piperidine alkaloids can be found in or extracted from ant venom or can be produced synthetically.

i. Extracts

Ant venom extracts can be made from ant venom or whole ants. For whole body extracts, insects can be ground to a fine texture, inserted into soluble capsules as whole body extract along with an edible carrier material such as fish oil, and are kept frozen until administration. The venom can be kept refrigerated in order to maintain its effectiveness. Additionally, each insect can contain approximately one venom unit or 40 nanoliters of the solenopsins, Solenopsin A and Solenopsin B.

ii. Chemical Synthesis

The present compounds can also be synthesized using general methods which are well known in the art. For examples, Wilkinson et al. reported a method for the enantioselective synthesis of 2,6-disubstituted piperidine alkaloids in *Org. Lett.* 2(2)155-8, 2000. Monfray et al. also reported a method for the synthesis of cis-2,6-disubstituted and 2,4,6-trisubstituted piperidine alkaloids (*Tetrahedron Asymm.* 16(5):1025-34, 2005). Hiroki et al. reported a method for the preparation of trans-2,6-disubstituted piperidine alkaloids (*Org. Biomol. Chem.* 4:1587-95, 2006). Still further examples are reported by Beak and Lee, who use Boc (tert-butoxycarbonyl) protected cyclic amines and convert them into 2,6-disubstituted piperidines (*J. Org. Chem.* 58:1109-1117, 1993). Further, Yamauchi et al. reported the reduction of (2-oxocyclohexyl) acetate with baker's yeast to provide an enantiomerically pure starting materials, which were then used to prepare 2,6-disubstituted piperidines (*Biosci. Biotechnol. Biochem.* 68(3): 676-84, 2004). Further examples of synthetic routes to 2,6-disubstituted piperidine alkaloids as disclosed herein can be found in, for example, Felpin et al. *Curr. Org. Syn.* 1:83-109, 2004; Comins et al. *J. Org. Chem.* 56:2506, 1991; and Wang et al. *J. Org. Chem.* 70:1897-1900, 2005. In yet another example, methods for preparing Solenopsin derivatives and analogous piperidine alkaloids are disclosed in U.S. Pat. No. 6,369,078. Each of these references is incorporated by reference herein in its entirety at least for its teachings of piperidine alkaloids and methods for preparing them.

Methods for the chemical synthesis of piperidine alkaloids such as solenopsins are disclosed in U.S. Patent Publication 2005/0038071, which is incorporated herein by reference in its entirety for the teaching of these compositions and methods. An efficient flexible chemistry can be used to synthesize Solenopsin A and analogues from Solenopsin A. Various methods can be used and adapted for a number of analogues disclosed herein.

See, for example, Comins, D. L., et al. (J. Org. Chem. 1991, 56, 2506), which is incorporated herein by reference for these teachings. For example, 4-chloropyridine can undergo introduction of an R group at the 2-position of the pyridine ring using alkylmagnesium bromide in THF at −78° C. followed by treatment with phenylchloroformate to provide the respective dihydropyridine derivative. The dihydropyridine derivative can then be converted into the corresponding N-Boc (Boc is a tertiary butyl carbonate group) derivative using potassium t-butoxide in tetrahydrofuran and −42° C. A methyl (or other alkyl group) can be introduced into the 6 position of the dihydropyridine ring by utilizing a first step of n-butyllithium (n-BuLi) in THF at −78° C. followed by introduction of the methyl (alkyl) group at the 6 position of the dihydropyridine compound utilizing methyliodide to form the dialkyl substituted chlorine substituted dihydropyridine derivative. The dialkyl substituted chorine substituted dihydropyridine derivative can then be subjected to a hydrogenation procedure (hydrogen, palladium/carbon catalyst in methanol) to remove the chlorine group at the 4 position, which derivative is further hydrogenated using $NABH_3/TFA$ in methylene chloride to provide the dialkyl substituted N-boc piperidine derivative. The boc group can be readily removed using 15% trifluoracetic acid in methylene chloride to afford the dialkyl substituted piperidine derivative. Salt formation can readily occur using the appropriate acid to acidify the basic nitrogen.

In an alternative chemical synthetic method, a more efficient route to the dialkyl Substituted piperidine analogues can be used. This route can allow the facile introduction of a double bond in the side chain of the 2 position of the piperidine ring. The method can follow the chemical methods reported by Beak, et al. (Beak, P.; Lee, W. K. J. Org. Chem. 1993, 58, 1109; Tetrahedron Lett. 1989, 30, 1197), which are incorporated herein by reference for the teaching of this synthetic method. This method demonstrated a regioselective and diastereoselective method for a lithiation-substitution at a methylene group.

N-boc piperidine can be subjected to sec-butyllithium (sec-BuLi) at −78° C. followed by dimethylsulfate to provide the methyl substituted N-Boc piperidine analog. The N-Boc piperidine analog prepared above can then be subjected to sec-BuLi at −78° C. followed by dimethyl formamide to produce the formyl piperidine derivative which can be further reacted using a Wittig procedure to produce longer chain alkylated products (saturated or unsaturated). If one desires an unsaturated side chain, the Wittig reaction can afford such a substituent directly, followed by removal of the Boc group using procedures. Salt formation may also readily occur, using standard methods available in the art.

Alternatively, to provide the alkyl (saturated) side chains, the Wittig product can be reduced using hydrogen/Pd/C to provide the fully saturated side chain. The Boc group can be readily removed using the previously described method, followed by salt formation.

The above-described methods of chemical synthesis can be readily adapted by those of ordinary skill to substitute different side chains at the 2 and 6 position of the piperidine ring to produce the disclosed compounds. These methods can be readily adapted to produce a large number of side chains for the disclosed compounds.

4. Method of Administering

The compositions may be administered orally, parenterally (e.g., intravenously), by intracranial injection, by intramuscular injection, by intraperitoneal injection, transdermally, extracorporeally, topically or the like, including topical intranasal administration or administration by inhalant. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. Another approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409, 1991).

5. Doses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

Following administration of a disclosed composition for treating, inhibiting, or preventing a neurological disease, the efficacy of the therapeutic can be assessed in various ways well known to the skilled practitioner. For instance, one of ordinary skill in the art will understand that a composition disclosed herein is efficacious in treating or inhibiting a neurological disease in a subject by evaluating cognitive function.

D. SPECIFIC EMBODIMENTS

Provided is a method of treating or preventing neurodegenerative disease in a subject comprising identifying a subject at risk for neurodegenerative disease and administering to the subject a therapeutically effective amount of a composition comprising a piperidine alkaloid. The composition can comprise an extract of fire ant (*Solenopsis invicta*) venom. The piperidine alkaloid can comprises the formula

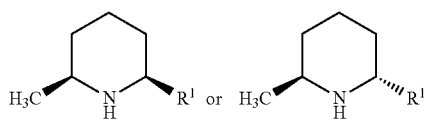

wherein R is n-alkyl-piperidine.

The piperidine alkaloid can comprises 2-methyl-6-alkyl-piperidine. The piperidine alkaloid can be Solenopsin A. The method piperidine alkaloid can be selected from the group consisting of cis-2-methyl-6-undecylpiperidine, trans-2-methyl-6-undecylpiperidine, cis-2-methyl-6-tridecylpiperidine, trans-2-methyl-6-tridecylpiperidine, cis-2-methyl-6-pentadecylpiperidine, trans-2-methyl-6-pentadecylpiperidine, cis-2-methyl-6-(cis-4-tridecen-1-yl)piperidine, trans-2-methyl-6-(cis-4-tridecen-1-yl)piperidine, cis-2-methyl-6-(cis-4-pentadecen-1-yl)piperidine, trans-2-methyl-6-(cis-4-pentadecen-1-yl)piperidine. The piperidine alkaloid can be 2-methyl-6-undecylpiperidine.

In one aspect, the subject has been diagnosed with Alzheimer's disease. The composition can be administered to the subject orally, systemically, or intracranially.

Also provided is a method of treating a subject at risk for Alzheimer's disease comprising administering to the subject a composition comprising a piperidine alkaloid.

E. EXAMPLES

1. Example 1

Animal Study

Fire ant venom (FAV) was extracted from *S. invicta* from Charleston, S.C. and transported in a Teflon beaker to prevent the ants from escaping. The ants were placed (n=100) in 30 ml vials containing hexane (5 ml). The vials were then sealed and the contents analyzed for the presence of FAV alkaloids after 24 h. The ants released their venom upon contact with the solvent.

Fire ant venom (FAV) extract was injected into aged rats (20 months) at several different doses (1, 10, and 100 ng/kg (i.p., daily). Animals were subjected to behavioral analysis using a Morris Water Maze and open-field testing after 7 days. Animals demonstrated a dose-dependent improvement in age-related deficits compared to vehicle injected animals. In addition, no adverse effects were seen in the animals at the doses given.

Example 2

Clinical Study

Mr. D. was an 86 year old, widowed, white male born in the U.S. Clinical Observations included 25 lb. weight loss, listless, restless, depressed, disorientation, and anxiety. Patient exhibited a significant decrease in cognitive functions, particularly in the areas of orientation (time, place, person), recent memory, new learning ability, digit span, information and vocabulary, calculating ability, and abstract thinking characteristic of mild to moderate Alzheimer's disease.

After serendipitous exposure to FAV (20-30 bites, 20-30 units/1 1) within a 48-72 hour window patient exhibited marked improvement in cognitive baseline, especially in the aforementioned areas; and in following this patient during the last year (with no maintenance dosing), although patient has demonstrated some cognitive regression he still remains markedly improved in cognitive abilities. In addition, all signs of depression are gone; he has gained 27 lbs. during that one-year time frame, goes to the gym four times per week, and has resumed an active social lifestyle among his elderly peer group. Friends and family have remarked about the remarkable turnaround in his life.

Patient presents a unique pristine pharmacological history as the only medication he was and is presently taking is 81 mg of aspirin per day.

Example 3

Behavioral Changes in APP Mice Chronically Treated with SPI-001 (Solenopsin A) at 10 mg/kg/Day for 90 Days. Morris Water Maze Test Based on chemical synthesis of SPI-001 and mass spec analysis, the compound has a molecular weight of <500. It is not a protein or peptide, but is a small molecule. SPI-001 is soluble in dimethyl sulfoxide (DMSO) and ethanol to 100 mg/ml. SPI-001 is slightly soluble in water. SPI-001 can be resuspended in 25% polyethylene glycol (PEG) 400 for oral delivery.

Initial studies suggest that SPI-001 inhibits MSK1 and CamK1δ while activating the MAPKAPK2 pathways and inhibiting Pl3 kinase. Recent CEREP screen indicated for SPI-001 (10 mM) that it inhibited muscarinic receptors (M1, M2 and M3), Na+ channels and monoamine (NE, DA, and 5-HT) transporters with high affinity (~90%).

Behavioral Analysis.

Morris water-maze testing. All mice were tested once in the Morris water maze test at the end of the experiment. Mice were trained in a 1.2 m open field water maze. The pool was filled to a depth of 30 cm with water and maintained at 25° C. The escape platform (10 cm square) was placed 1 cm below the surface of the water. During the trials, the platform was removed from the pool. The cued test was carried out in the pool surrounded with white curtains to hide any extra-maze cues. All animals underwent non-spatial pretraining (NSP) for three consecutive days. These trials were to prepare the animals for the final behavioral test to determine the retention of memory to find the platform. These trials were not recorded (for training purposes only). For the training and learning studies, the curtains were removed to add extra-maze cues (this allows for the identification of animals with swimming impairments). On day 1, the mice were placed on the hidden platform for 20 seconds (trial 1), for trials 2-3 animals were released in the water at a distance of 10 cm from the cued-platform or hidden platform (trial 4) and allowed to swim to the platform. On the second day of trials, the hidden platform was moved randomly between the center of the pool or the center of each quadrant. The animals were released into the pool, randomly facing the wall and will be allowed 60 seconds to reach the platform (3 trials). In the third trial, animals were given three trials, two with a hidden platform and one with a cued platform. Two days following the NSP, animals were subjected to final behavioral trials (Morris water maze test). For these trials (3 per animal), the platform was placed in the center of one quadrant of the pool and the animals released facing the wall in a random fashion. The animal was allowed to find the platform or swim for 60 seconds (latency period, the time it takes to find the platform). Animals were tested on days 86-88 for the non-spatial pretraining and the final trials were performed on day 90. See FIG. 1.

Example 4

In Vivo Effect on Brain and Plasma Aβ Peptide Levels after Single Administration of SPI-001 at 10 Mg/Kg in 25% PEG 400 or 25% PEG 400 Orally The APP mice (male) used in these experiments were designed by microinjection of the human APP gene (with the Swedish and London mutations) into mouse eggs under the control of the platelet-derived growth factor B (PDGF-B) chain gene promoter. The mice were generated on a C57BL/6 background. Animals were housed in the Medical University of South Carolina Animal Facility under a 12:12 light:dark cycle. Animals were housed in standard non-sterile rodent microisolator cages, with filtered cage tops and housed 4 to a cage. Animals were fed ad libitum and maintained by brother sister mating. Transgenic animals were identified by PCR analysis. The mice generated from this construct develop amyloid deposits starting at 3 months of age. Animals were aged for 3 months and then maintained for 90 days and sacrificed for amyloid quantification.

Figure 2:
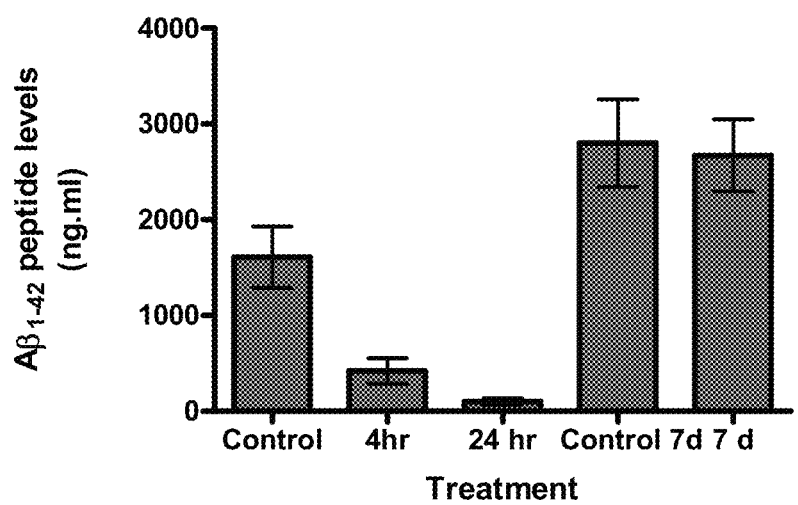
FIG. 2 shows A$\beta$1-42 peptide analysis in the brain of APP transgenic mice treated with SPI-001 at 10 mg/kg in 25% PEG 400 for the indicated times.
Figure 3:
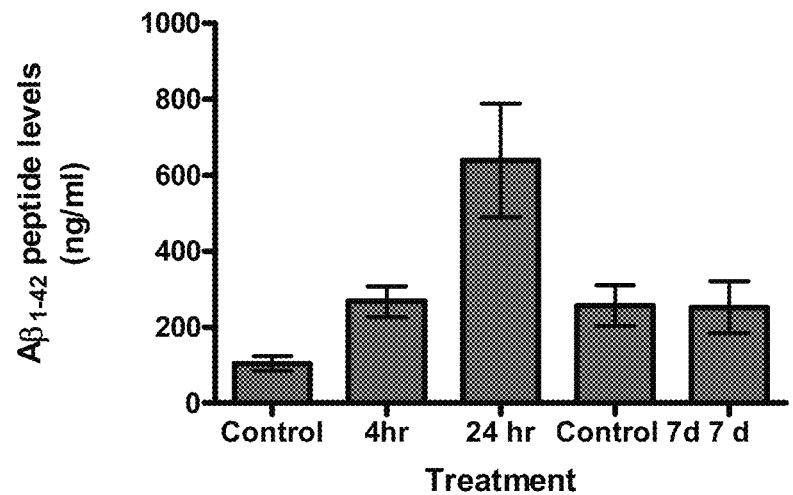
FIG. 3 shows A$\beta$1-42 peptide analysis in the plasma of APP transgenic mice treated with SPI-001 at 10 mg/kg in 25% PEG 400 for the indicated times.

FIG. 2 illustrates the effect of SPI-001 on brain $A\beta_{1-42}$ peptide levels when administered at 10 mg/kg orally to the APP transgenic mice. Animals were dosed once with SPI-001 and then examined at 0, 4, 24 hours and 7 days for A peptide levels (Biosource International). As seen in the figure, $A\beta_{1-42}$ peptide levels decreased within 4 hr and continued to decrease out to 24 hours. Levels returned to control levels by 7 days. As seen in FIG. 3, plasma $A\beta_{1-42}$ peptide levels increased within 4 hr and continued to increase out to 24 hours. Levels returned to control levels by 7 days. $A\beta_{1-40}$ peptide levels showed the same levels of decrease in the brain and increase in the plasma. The plasma levels were opposite to the brain levels.

Example 5

Single Administration of SPI-001 at 10 Mg/Kg in 25% PEG 400 or 25% PEG 400 Orally (APP Mice)

Figure 4:
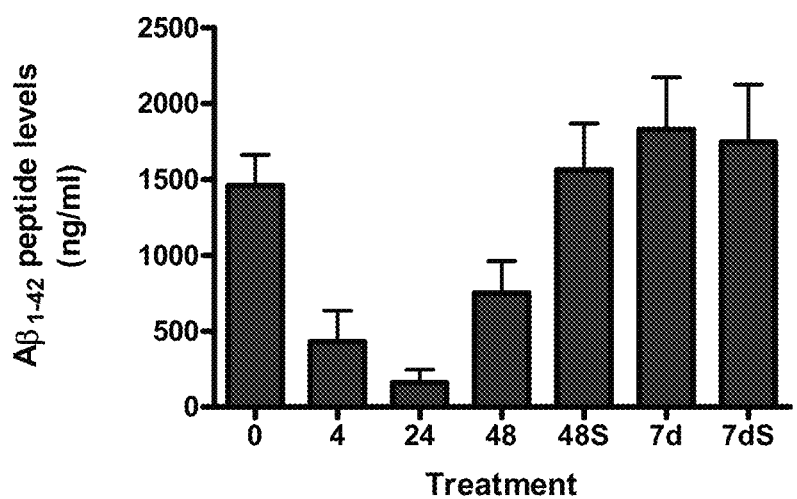
FIG. 4 shows A$\beta$1-42 peptide analysis in the brain of APP transgenic mice treated with SPI-001 at 10 mg/kg in 25% PEG 400 for the indicated times. 48S and 7dS indicate treatment of animals with 25% PEG alone.

Animals were dosed once with SPI-001 and then examined at 0, 4, 24, 48 hours and 7 days for A peptide levels. As seen in FIG. 4, $A\beta_{1-42}$ peptide levels decreased within 4 hr and continued to decrease out to 24 hours. Levels returned to control levels by 48 hours and 7 days. As with the 10 mg/kg studies, plasma $A\beta_{1-42}$ peptide levels in the 10 mg/kg animals increased within 4 hr and continued to increase out to 24 hours. Levels returned to control levels by 48 hours and 7 days. $A\beta_{1-40}$ peptide levels showed the same levels of decrease in the brain and increase in the plasma. The plasma levels were opposite to the brain levels.

Example 6

Single Administration of SPI-001 at 10 Mg/Kg in 25% PEG 400 or 25% PEG 400 Orally (Guinea Pigs)

As also seen in our mouse studies, SPI-001 showed a decrease in brain $A\beta_{1-42}$ peptide levels in the Guinea Pig when administered at 10 mg/kg orally. Animals were dosed once with SPI-001 and then examined at 0, 4, 24, 48 hours and 7 days for Aβ peptide levels. As seen in FIG. 4, $A\beta_{1-42}$ peptide levels decreased within 4 hr and continued to decrease out to 24 hours. Levels returned to control levels by 48 hours and 7 days. Plasma $A\beta_{1-42}$ peptide levels increased within 4 hr and continued to increase out to 24 hours. Levels returned to control levels by 48 hours and 7 days. $A\beta_{1-40}$ peptide levels showed the same levels of decrease in the brain and increase in the plasma.

Example 7

Figure 5:
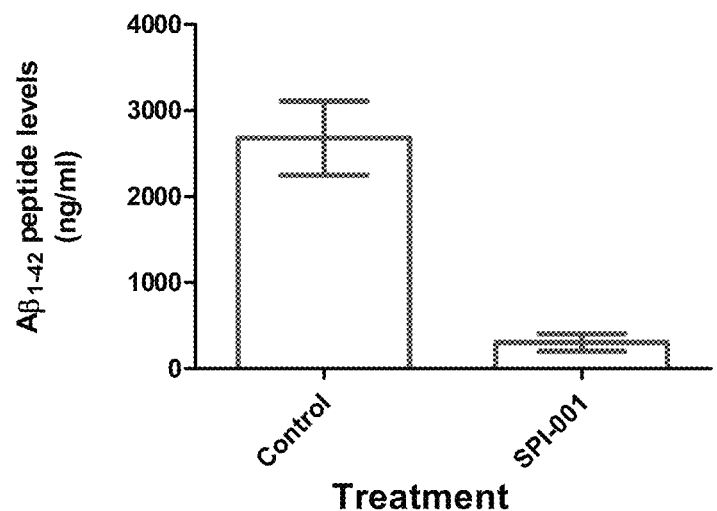
FIG. 5 shows A$\beta$1-42 peptide analysis in the brain of APP transgenic mice treated with SPI-001 at 10 mg/kg in 25% PEG 400 for 7 days.
Figure 6:
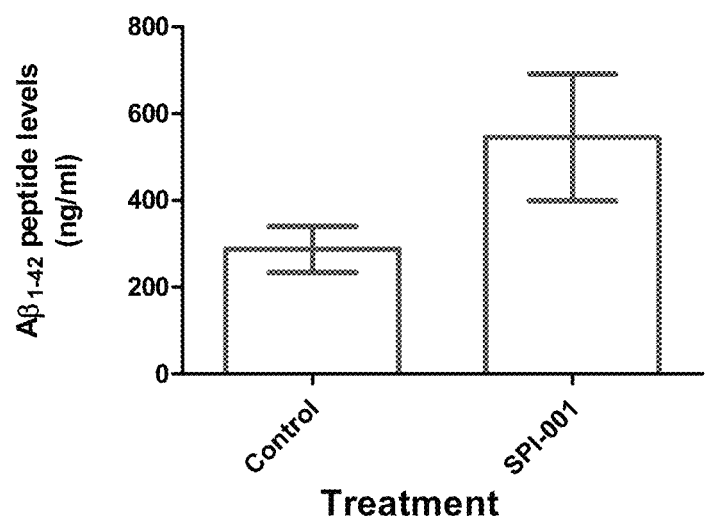
FIG. 6 shows A$\beta$1-42 peptide analysis in the plasma of APP transgenic mice treated with SPI-001 at 10 mg/kg in 25% PEG 400 for 7 days.

Acute Administration of SPI-001 at 10 Mg/Kg for 7 Days in 25% PEG 400 or 25% PEG 400 Alone Animals were dosed once with SPI-001 and then examined at 7 days for Aβ peptide levels. As seen in FIG. 5, $A\beta_{1-42}$ peptide levels were decreased at 7 days compared to control animals given 25% PEG only. As seen in FIG. 6, plasma $A\beta_{1-42}$ peptide levels were increased compared to control levels at 7 days.

Example 8

Repetitive Administration of SPI-001 at 10 mg/kg

Figure 7:
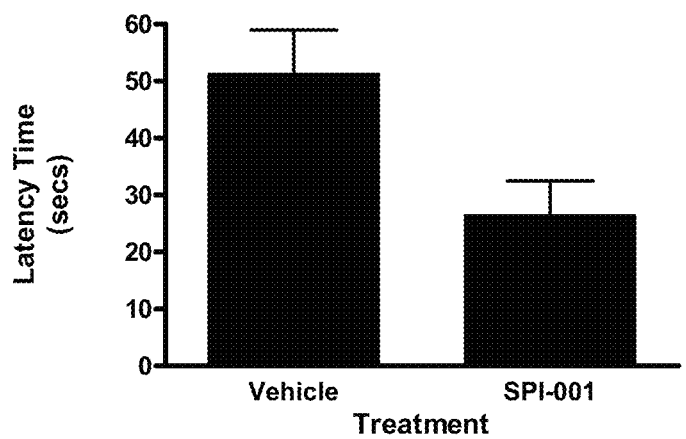
FIG. 7 shows behavioral changes in APP mice treated with 10 mg/kg SPI-001 for 90 days. Effects of SPI-001 on latency time to find hidden platform (Morris water maze).
Figure 8:
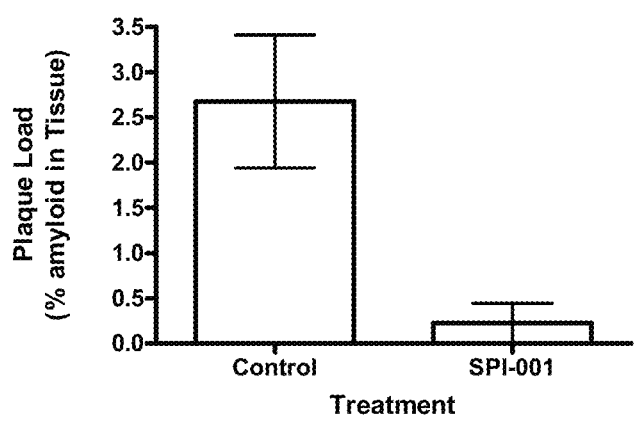
FIG. 8 illustrates the plaque load in the brains of control and SPI-001 treated animals.

SPI-001 was administered to APP transgenic mice at 10 mg/kg for 3 months to determine the effect upon Aβ peptide and amyloid load. Animals were administered SPI-001 orally in 25% PEG daily and examined for abnormal pathology. Animals did not show any signs of systemic pathological features (liver, kidney, heart, lungs, intestine). Animals were analyzed for behavioral changes associated with drug treatment (FIG. 7). As seen in the figure, the mice treated with SPI-001 showed an improvement in behavior in the Morris Water Maze. Additionally, when mice were sacrificed and examined for amyloid load and Aβ peptide levels, both were significantly reduced compared to the control animals. FIG. 8 illustrates the plaque load in the brains of control and SPI-001 treated animals.

Example 9

Animals were Sacrificed and Examined for Aβ Peptide Levels in the Brain

Figure 9:
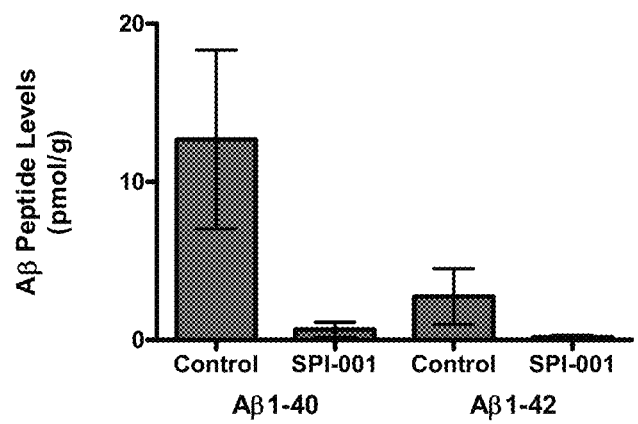
FIG. 9 shows A$\beta$ peptide levels in the brain following treatment with SPI-001.

See FIG. 9.

Example 10

PK Profile

Figure 10:
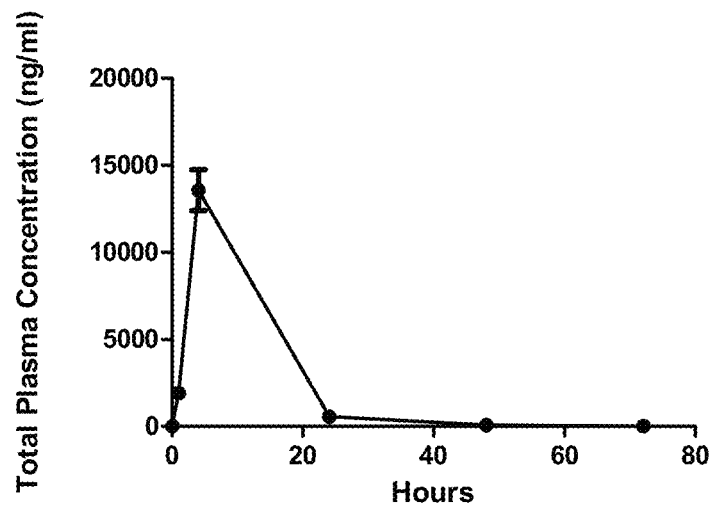
FIG. 10 shows the PK profile of SPI-001 in plasma after APP transgenic animals were orally administered SPI-001 at 10 mg/kg.
Figure 11:
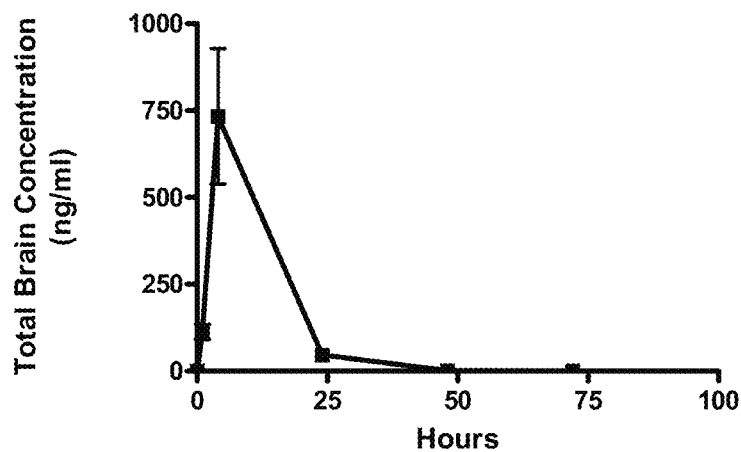
FIG. 11 shows the PK profile of SPI-001 levels in brain after APP transgenic animals were orally administered SPI-001 at 10 mg/kg.

For PK profile, the APP transgenic animals were administered SPI-001, and blood samples and brain tissue were collected and subjected to drug analysis. As seen in FIGS. 10 and 11, SPI-001 levels increased significantly in the plasma and brain quickly and were maintained for approximately 24 hours.

Example 11

Selectivity and Safety Profile

Figure 12:
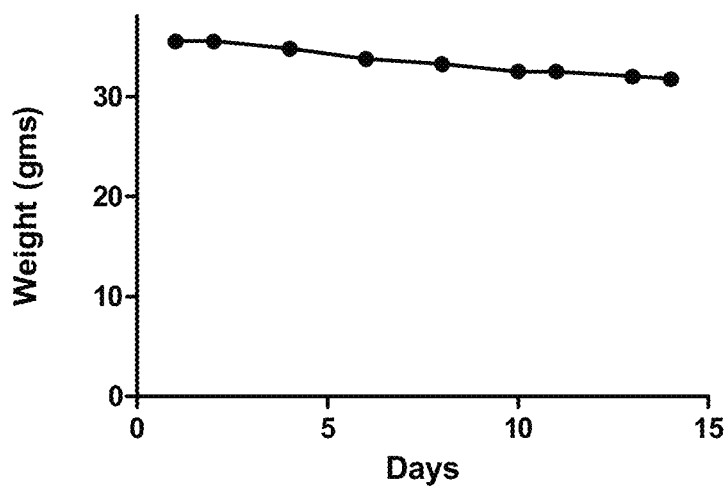
FIG. 12 shows weight analysis of animals subjected to 14-day treatment with SPI-001.

Animals (C57BL/6 mice, 5 mice per group) were treated with SPI-001 at 0, 4, 40, and 400 mg/kg in 25% PEG 400 with a single dose and examined 14 days later. The animals demonstrated no gross behavioral deficits upon visual inspection (daily) and histological analysis of the tissues (brain, liver, kidney, heart, intestine, and lungs, did not show any abnormal structures). A second treatment with SPI-001 at 400 mg/kg in 25% PEG 400 for 14 days showed no gross behavioral deficits, and no histological abnormalities in the tissues examined. The animals did display a slight decrease in body weight over the 14 days (FIG. 12). Animals treated with 25% PEG showed a similar profile compared to the SPI-001 treated animals. The body weight changes stopped by 14 days and reversed.

What is claimed is:

1. A method of treating a human subject diagnosed with neurodegenerative disease comprising administering to a human subject diagnosed with neurodegenerative disease a therapeutically effective amount of a composition comprising a piperidine alkaloid, wherein the piperidine alkaloid comprises the formula:

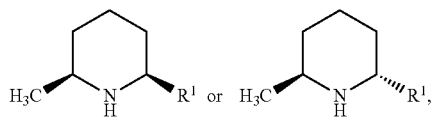

wherein $R^1$ is a substituted or unsubstituted aliphatic group having from 7 to 30 carbon atoms.

2. The method of claim 1, wherein the composition comprises an extract of fire ant (*Solenopsis invicta*) venom.

3. The method of claim 1, wherein the piperidine alkaloid is Solenopsin B.

4. The method of claim 1, wherein the piperidine alkaloid is selected from the group consisting of cis-2-methyl-6-undecylpiperidine, cis-2-methyl-6-tridecylpiperidine, cis-2-methyl-6-pentadecylpiperidine, cis-2-methyl-6-(cis-4-tridecen-1-yl)piperidine, trans-2-methyl-6-(cis-4-tridecen-1-yl)piperidine, cis-2-methyl-6-(cis-4-pentadecen-1-yl)piperidine, trans-2-methyl-6-(cis-4-pentadecen-1-yl)piperidine.

5. The method of claim 1, wherein the piperidine alkaloid is 2-methyl-6-undecylpiperidine.

6. The method of claim 1, wherein the subject has been diagnosed with Alzheimer's disease.

7. The method of claim 1, wherein the composition is administered to the subject orally, systemically, or intracranially.

8. A method of treating a human subject at risk for Alzheimer's disease comprising administering to the subject a composition comprising a piperidine alkaloid, wherein the piperidine alkaloid comprises the formula:

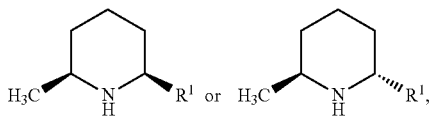

wherein $R^1$ is a substituted or unsubstituted aliphatic group having from 7 to 30 carbon atoms.

* * * * *